US012747651B2

(12) United States Patent
Craddock et al.

(10) Patent No.: US 12,747,651 B2
(45) Date of Patent: Sep. 29, 2026

(54) SYSTEMS AND METHODS FOR DETERMINING REACTIVITY INDICES FOR CARBON DIOXIDE SEQUESTRATION

(71) Applicant: Schlumberger Technology Corporation, Sugar Land, TX (US)

(72) Inventors: Paul Ryan Craddock, Cambridge, MA (US); Jeffrey Miles, Cambridge, MA (US); Laurent Mosse, Bucharest (RO)

(73) Assignee: Schlumberger Technology Corporation, Sugar Land, TX (US)

( * ) Notice: Subject to any disclaimer, the term of this patent is extended or adjusted under 35 U.S.C. 154(b) by 311 days.

(21) Appl. No.: 18/635,496

(22) Filed: Apr. 15, 2024

(65) Prior Publication Data

US 2025/0320791 A1 Oct. 16, 2025

(51) Int. Cl.

| | |
|---|---|
| ***E21B 41/00*** | (2006.01) |
| ***E21B 49/00*** | (2006.01) |
| ***G01N 33/24*** | (2006.01) |

(52) U.S. Cl.

CPC ........ *E21B 41/0064* (2013.01); *E21B 49/005* (2013.01); *G01N 33/24* (2013.01); *Y02C 20/40* (2020.08)

(58) Field of Classification Search

None

See application file for complete search history.

(56) References Cited

U.S. PATENT DOCUMENTS

| | | | |
|---|---|---|---|
| 2023/0152254 | A1 | 5/2023 | Chen |
| 2024/0110464 | A1 | 4/2024 | Skeels |

FOREIGN PATENT DOCUMENTS

| | | | |
|---|---|---|---|
| EP | 4219889 | A1 | 8/2023 |
| WO | 2024035923 | A1 | 2/2024 |

OTHER PUBLICATIONS

Ajayi T. A review of CO2 storage in geological formations emphasizing modeling, monitoring and capacity estimation approaches. Petroleum Science 16: 1028-1063. (Year: 2019).*

Zhang Y. Simulation of CO2 storage using a parameterization method for essentia trapping physics: FluidFlower benchmark study. bioRxiv arXiv 2301.08004v1, 20 pgs. (Year: 2023).*

Cui, G. et al., "Geochemical reactions and their effect on CO2 storage efficiency during the whole process of CO2 EOR and subsequent storage", International Journal of Greenhouse Gas Control, 2021, 108, 12 pages.

Mayer, C. et al., "Global, A New Approach to Computer-Processed Log Interpretation", SPE Annual Technical Conference and Exhibition, SPE-9341-MS, Sep. 21, 1980, pp. 1-14.

Herron, M. et al. , "Quantitative Lithology: Open and Cased Hole Application Derived From Integrated Core Chemistry and Mineralogy Database", Geological Society London Special Publications, Aug. 1998, pp. 81-95, vol. 136, No. 1.

Craddock, P.R. et al., "Enhanced Mineral Quantification And Uncertainty Analysis From Downhole Spectroscopy Logs Using Variational Autoencoders", Petrophysics, Dec. 1, 2021, pp. 614-629, vol. 62, No. 06.

Craddock, P.R. et al., "Comparison of Quantitative Mineral Analysis By X-Ray Diffraction and Fourier Transform Infrared Spectroscopy" Journal of Sedimentary Research, Jun. 2017, pp. 630-652, vol. 87, No. 6.

* cited by examiner

*Primary Examiner* — Olivia M. Wise

*Assistant Examiner* — Robert J. Kallal

(74) *Attorney, Agent, or Firm* — Jeffrey D. Frantz

(57) ABSTRACT

Provided herein are methods of determining the reactivity of one or more minerals present within a geological formation within a target zone in response to the injection of $CO_2$ into the target zone. For example, the methods may comprise one or more of the following steps: (1) determining one or more mineral and fluid characteristics of a geological formation comprising one or more minerals; (2) using a reaction rate model to characterize the chemical reactivity of one or more minerals present in a target zone of the geological formation in response to injection of $CO_2$ into the target zone; (3) using a reactivity index model to estimate the amount of one or more minerals in the target zone that would be modified between a first time point and a second point during a $CO_2$ injection and sequestration operation; and (4) injecting an amount of $CO_2$ into the target zone based on the estimated reactivity of the one or more minerals present in the target zone.

10 Claims, 1 Drawing Sheet

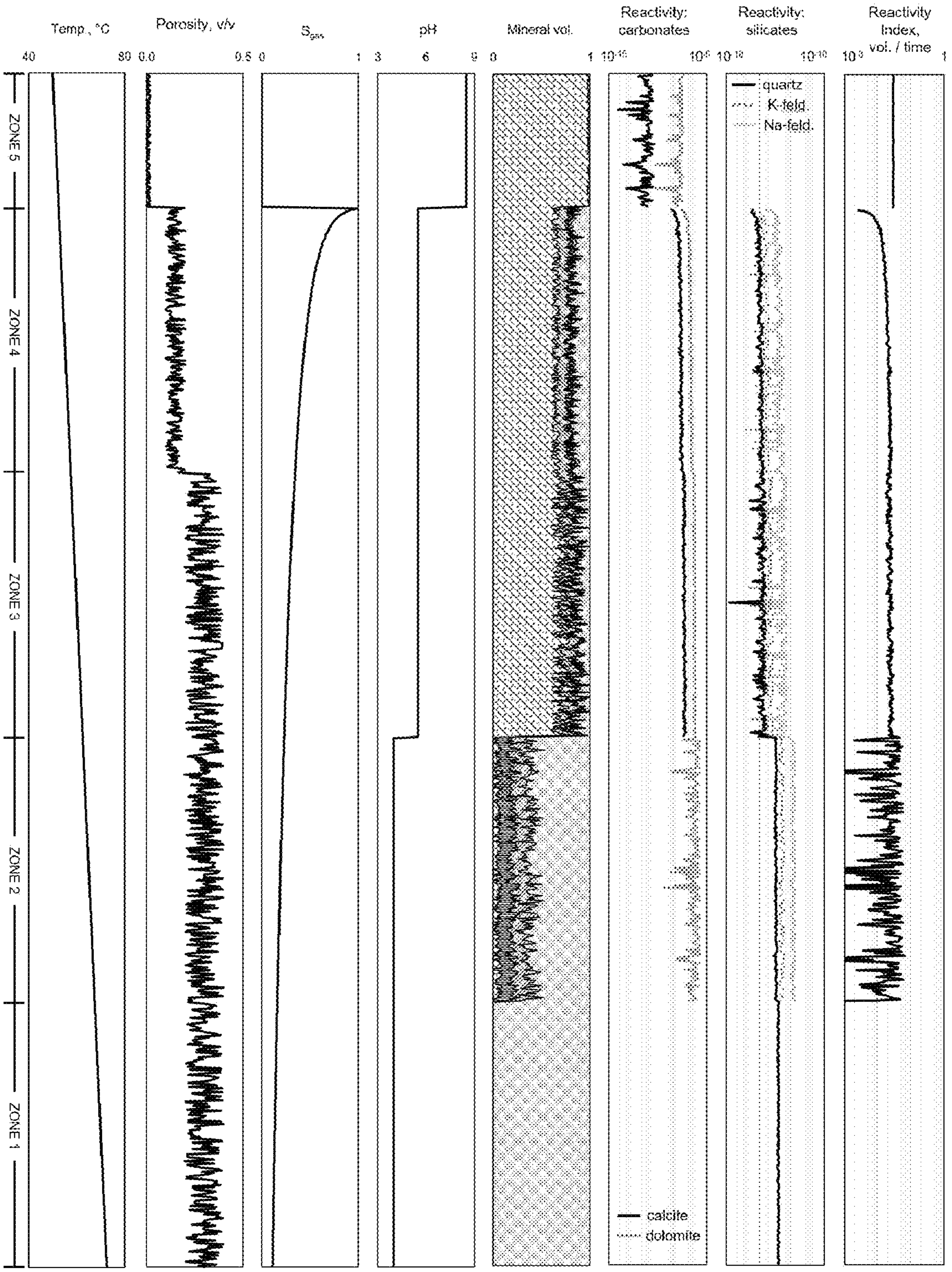
Temp., °C
40
80
Porosity, v/v
0.0
0.5
$S_{gas}$
0
1
pH
3
6
9
Mineral vol.
0
1
Reactivity: carbonates
Reactivity: silicates
quartz
K-feld.
Na-feld.
Reactivity Index, vol. / time
1
ZONE 5
ZONE 4
ZONE 3
ZONE 2
ZONE 1
calcite
dolomite

SYSTEMS AND METHODS FOR DETERMINING REACTIVITY INDICES FOR CARBON DIOXIDE SEQUESTRATION

TECHNICAL FIELD

This disclosure generally relates to systems and methods for characterizing geological formations. More particularly, the disclosure relates to a system and method for collecting, preparing, and analyzing data relating to the characteristics of one or more geological formations and determining a preferred geological formation for injecting carbon dioxide into.

BACKGROUND

The concentration of gaseous carbon dioxide ($CO_2$) in atmospheres is naturally regulated by planetary geological processes forming a global carbon cycle. However, $CO_2$ is a known greenhouse gas that contributes to radiative forcing of the Earth's atmosphere. Indeed, anthropogenic activities within the past century have contributed to $CO_2$ levels in the Earth's atmosphere that exceed the levels that the natural global carbon cycle can remove from the atmosphere. Thus, the increasing concentration of $CO_2$ in the Earth's atmosphere is recognized as a concern for the state of the Earth's current climate. Accordingly, various methods have been suggested to abate the increase of $CO_2$ in the Earth's atmosphere or the resulting radiative forcing.

Some conventional methods for decreasing the amount of $CO_2$ released to the Earth's atmosphere include carbon capture and storage (e.g., CCS), which is the capture, transport, compression, and sequestration of $CO_2$ into porous and permeable underground geological rock formations. Non-limiting examples of geological formations that can be used for CO2 sequestration include sedimentary sandstones (e.g., arenite, sub-arkose, arkose), sedimentary carbonates (e.g., limestone, dolostone), sedimentary siltstones and mudstones (e.g., shale), and mafic and ultramafic igneous formations (e.g., basalt, peridotite).

$CO_2$ can be captured from a point source of an atmospheric emission (e.g., an industrial facility) and/or directly from the atmosphere (e.g., direct air capture). Storage, or sequestration, of $CO_2$ includes the injection of the $CO_2$ into a suitable underground geological formation via a borehole drilled into the geological formation.

There is a need for improved systems and methods for analyzing and determining the type and extent of one or more chemical reactions that occur in a geological formation in response to the injection of $CO_2$.

SUMMARY

For example, provided herein is a method for determining the reactivity of one or more minerals present within a geological formation within a target zone in response to the injection of $CO_2$ into the target zone, the method comprising: (1) determining one or more mineral and fluid characteristics of the geological formation comprising one or more minerals; and (2) using a reaction rate model to characterize a chemical reactivity of one or more minerals present in the target zone of the geological formation in response to injection of $CO_2$ into the target zone.

Also provided herein is a method for determining the reactivity of one or more minerals present within a geological formation within a target zone in response to the injection of $CO_2$ into the target zone, the method comprising: (1) determining one or more mineral and fluid characteristics of the geological formation comprising one or more minerals; (2) using a reaction rate model to characterize the chemical reactivity of one or more minerals present in the target zone of the geological formation in response to injection of $CO_2$ into the target zone; (3) using a reactivity index model to estimate an amount of one or more minerals in the target zone that would be modified between a first time point and a second point during a $CO_2$ injection and sequestration operation; and (4) injecting an amount of $CO_2$ into the target zone based on the chemical reactivity of the one or more minerals present in the target zone.

Other objects and features will be in part apparent and in part pointed out hereinafter.

DESCRIPTION OF THE DRAWINGS

FIG. 1 depicts an example of using a reactivity index derived from borehole measurements to select one or more target zones for a CCS operation, as further described in Example 1.

DETAILED DESCRIPTION

Provided herein are systems and methods for analyzing and determining the type and extent of one or more chemical reactions that occur in a geological formation in response to the injection of $CO_2$.

For example, provided herein is a system for collecting and determining at least one geological formation input relating to geophysical and geochemical properties of the geological formation. Further provided herein is a method of analyzing the at least one geological formation input based on thermophysical and thermodynamic principles to determine a value or metric representing the reactivity of a geological formation to chemical disequilibria created by the injection of $CO_2$ into the geological formation.

The suitability of a geological formation for sequestering $CO_2$ can depend on various physical factors of the geological formation. One example of a physical factor is the geological formation's injectivity, which refers to the rate at which $CO_2$ can be injected into the geological formation without damaging the geological formation. Another example of a physical factor is the geological formation's capacity, which refers to the total effective pore volume of the formation and the mass of $CO_2$ that may be stored within the geological formation. Yet another example of a physical factor is the geological formation's security or containment, which refers to the likelihood that the injected $CO_2$ will remain within the geological formation and not otherwise escape to another location, such as another geological formation or the Earth's atmosphere.

The physical state of the injected $CO_2$ may be in a subcritical gas or liquid phase, a supercritical state, or as an aqueous solute. For example, Formula 1 illustrates an equilibrium between $CO_2$ in its gaseous and aqueous phases.

Formula 1

$$CO_2(g) \leftrightarrow CO_2(aq)$$

$CO_2$ is relatively chemically unreactive in the gas phase (g) but chemically reactive in the aqueous phase (aq). Thus, $CO_2$ dissolved in water can dissociate into various inorganic carbonate species. Accordingly, Formula 2 and Formula 3 illustrate the dissociation of aqueous $CO_2$.

Formula 2

$$CO_2(aq) + H_2O(aq) \leftrightarrow H_2CO_3(aq) \leftrightarrow H^+ + HCO_3^-$$

Formula 3

$$HCO_3^- \leftrightarrow H^+ + CO_3^{2-}$$

The species $H_2CO_3(aq)$ in Formula 2 is generally negligible with respect to the abundance of other inorganic carbon species. Accordingly, in Formula 2, $H_2CO_3(aq)$ is represented as an intermediary between $CO_2(aq)$ and $HCO_3^-$. Further, as demonstrated in Formula 2 and Formula 3, the acidic compound ($H^+$) drives various chemical reactions among gaseous, aqueous, and solid phases of compounds present in geological formations.

For example, Formula 4 demonstrates how acidity in the form of $H^+$ can promote the dissolution of the feldspar mineral oligoclase. For simplicity, Formula 4 is expressed with the reaction products $Na^+$, $Ca^{2+}$, and $Al^{3+}$ existing as aqueous-free ions. However, $Na^+$, $Ca^{2+}$, and $Al^{3+}$ can equally exist as aqueous complexes, depending on the overall chemical system.

Formula 4

$$Na_{0.8}Ca_{0.2}Al_{1.2}Si_{2.8}O_8 + 4.8H^+ \leftrightarrow 0.8Na^+ + 0.2Ca^{2+} + 1.2Al^{3+} + 2.8SiO_2(aq) + 2.4H_2O(aq)$$

Further, bicarbonate ($HCO_3^-$) and carbonate ($CO_3^{2-}$) species can react with aqueous cations to form aqueous carbonate complexes as well as solid carbonate compounds.

In one example, Formula 5 demonstrates how a divalent cation ($M^{2+}$) reacts with bicarbonate to form an aqueous carbonate complex. $M^{2+}$ can be $Ca^{2+}$, $Mg^{2+}$, or $Fe^2$.

Formula 5

$$M^{2+} + 2HCO_3^- \leftrightarrow MCO_3(s) + CO_2(aq) + H_2O(aq)$$

In another example, Formula 6 demonstrates how a divalent cation ($M^{2+}$) reacts with bicarbonate to form a solid carbonate complex. $M^{2+}$ can be $Ca^{2+}$, $Mg^{2+}$, or $Fe^2$.

Formula 6

$$M^{2+} + HCO_3^- \leftrightarrow MCO_3(s) + H^+$$

In yet another example, Formula 7 demonstrates how a divalent cation ($M^{2+}$) reacts with carbonate to form a solid carbonate compound. $M^{2+}$ can be $Ca^{2+}$, $Mg^{2+}$, or $Fe^2$.

Formula 7

$$M^{2+} + CO_3^{2-} \leftrightarrow MCO_3(s)$$

Thus, it can be determined that the injection of $CO_2$ into subterranean geological formations can disturb the chemical state within that geological formation. Accordingly, the injection of $CO_2$ into a geological formation can lead to gas-liquid-solid reactions that can affect the long-term injectivity, capacity, and containment of CO2 sequestered in that geological formation.

Mineral dissolution caused by the injection of $CO_2$ into a geological formation can be beneficial to CCS field operations. In some examples, mineral dissolution is beneficial because mineral dissolution can increase the porosity of the geological formation by increasing the capacity of the geological formation. In another example, mineral dissolution can be beneficial to CCS field operations because mineral dissolution can increase the permeability of the geological formation by increasing the injectivity of the geological formation.

However, in other instances, mineral dissolution caused by the injection of $CO_2$ into a geological formation can be detrimental to CCS field operations. In some examples, mineral dissolution is detrimental to CCS field operations because mineral dissolution can increase the likelihood of $CO_2$ leakage from the geological formation by reducing the containment of the geological formation.

Further, mineral precipitation caused by the injection of $CO_2$ into a geological formation can be beneficial to CCS field operations. In some examples, mineral precipitation is beneficial because mineral precipitation can decrease the likelihood of $CO_2$ leakage through adjacent geological formations by increasing the porosity of the geological formation where the $CO_2$ was injected into.

Conversely, mineral precipitation caused by the injection of $CO_2$ into a geological formation can be detrimental to CCS field operations. In some examples, mineral precipitation is detrimental because mineral precipitation can decrease the geological formation's porosity and permeability which can decrease the geological formation's ability to store $CO_2$.

Moreover, the thermophysical, geophysical, and geochemical properties of a geological formation can be influenced by the type and abundance of minerals in the geological formation. Thus, the amount of solid minerals in geological formation caused by mineral dissolution and/or mineral precipitation due to CO2 injection can impact the injectivity and capacity of the geological formation.

Further, the amount of solid minerals in the geological formation can dynamically change during a CCS operation. Therefore, it is advantageous to predict, anticipate, or quantify the type and extent of certain chemical reactions that can change the solid mineral content in a geological formation so that the usefulness of the geological formation for CCS can be assessed.

Determining Characteristics of a Geological Formation

When drilling through a geological formation or other formations for oil, natural gas, or other materials, it is beneficial to determine or estimate the type of geological formation that is being drilled through because the geological formation type can be used to estimate the geological formation's porosity, water saturation, net hydrocarbon content, and permeability and production rates. The geological formation type can also be useful in making drilling decisions based on the estimated mechanical properties of the geological formation.

The geological formation type can be defined by one or more thermophysical, geophysical, and geochemical properties of the geological formation. Thus, provided herein are systems and methods for collecting and determining at least one geological formation input relating to a geological formation's thermophysical, geophysical, and geochemical properties.

Geological Formation Inputs

Non-limiting examples of geological formation inputs include a mineral make-up, one or more mineral concentrations (e.g., mole fraction, mass fraction, or volume fraction), a mineral surface area, a pore volume, a pore surface area, a pore-size distribution, an electromagnetic resistivity, one or more dielectric properties, imaging data, and acoustic properties of the geological formation, and a composition of the CCS injection fluid.

The mineralogical assemblage in the geological formation (e.g., the mineral make-up of the geological formation) can be determined from well-log interpretation models described herein using data acquired from one or more borehole logging measurements performed within a borehole traversing the geological formation.

Non-limiting examples of rock-forming minerals for sedimentary geological formations (e.g., sedimentary sandstones, sedimentary carbonates, and sedimentary siltstones and mudstones) include quartz, potassium feldspar, plagioclase feldspar, calcite, dolomite, ankerite, siderite, anhydrite, pyrite, illite-clay, smectite-clay, kaolinite-clay, chlorite-clay, and mica.

Non-limiting examples of rock-forming minerals for igneous geological formations (e.g., mafic and ultramafic igneous formations) include olivine (i.e., forsterite-fayalite solid solution), orthopyroxene (i.e., enstatite-ferrosilite solid solution), clinopyroxene (e.g., diopside, augite, pigeonite).

Non-limiting examples of rock-forming minerals for metamorphic geological formations include sillimanite, kyanite, staurolite, andalusite, and garnet.

In some examples, the well-log interpretation model for determining the mineralogical assemblage of the geological formation can include a maximum likelihood model using a resistivity value, a porosity value, a natural gamma ray value, an electromagnetic propagation value, a thermal-neutron decay rate, a spontaneous potential value, and/or a logging combination value. See, Mayer, C., and A. Sibbit. "Global, A New Approach to Computer-Processed Log Interpretation." Paper presented at the SPE Annual Technical Conference and Exhibition, Dallas, Texas, September 1980. doi: https://doi.org/10.2118/9341-MS.

In some examples, the well-log interpretation model for determining the mineralogical assemblage of the geological formation can include an elements-to-minerals model using geochemical spectroscopy logs. See, Herron, Michael & Herron, Susan. (1998). Quantitative lithology: Open and cased hole application derived from integrated core chemistry and mineralogy database. Geological Special Society, London, Publications. 136. 81-95. 10.1144/GSL.SP.1998.136.01.08. See also, Craddock, Paul R., Srivastava, Prakhar, Datir, Harish, Rose, David, Zhou, Tong, Mosse, Laurent, and Lalitha Venkataramanan. "Enhanced Mineral Quantification and Uncertainty Analysis from Downhole Spectroscopy Logs Using Variational Autoencoders." Petrophysics 62 (2021): 614-629. doi: https://doi.org/10.30632/PJV62N6-2021a2.

In another example, a mass-fraction abundance of each mineral in the geological formation can be determined from laboratory measurements.

In one example, the laboratory measurements can be obtained using X-ray diffraction.

In another example, the laboratory measurements can be obtained using infrared spectroscopy techniques. See, Paul R. Craddock, Michael M. Herron Susan L. Herron; "Comparison of Quantitative Mineral Analysis by X-Ray Diffraction and Fourier Transform Infrared Spectroscopy," Journal of Sedimentary Research 2017; 87 (6): 630-652. doi: https://doi.org/10.2110/jsr.2017.34

The geological formation porosity can be inferred from various petrophysical well logs. Non-limiting examples of well logs include a bulk density log, a neutron porosity log, and a nuclear magnetic resonance log.

Pore-size distribution and/or pore surface area can be inferred from nuclear magnetic resonance measurements or from combined knowledge of the geological formation's mineral concentrations, mineral surface areas, and porosity.

Chemical compositions of the CCS fluid can be measured using spectroscopy techniques. Non-limiting examples of spectroscopy techniques include MS, AAS, and AES. In some examples, the spectroscopy data is analyzed in combination with fluid properties determinable from downhole well logs, formation sampling, and sample testing measurements.

Collecting Geological Formation Samples

The at least one geological formation input described herein can be determined from a geological formation sample.

Non-limiting examples of the geological formation sample include a rock chip, a rock core, a rock drill cutting, a rock outcrop, a sample from a rock formation surrounding a borehole, and combinations thereof.

In some examples, the geological formation sample is analyzed during or after the formation of a borehole. In some examples, the geological formation sample is analyzed along a depth of the borehole. A non-limiting example of a method for analyzing the geological formation sample via the borehole includes a logging while drilling (e.g., LWD) method. LWD is the measurement of the geological formation properties (e.g., geological formation inputs) during the excavation of the borehole or shortly thereafter through the use of tools and/or sensors integrated into a bottomhole assembly. Another non-limiting example of a method for analyzing the geological formation sample via the borehole includes a wireline logging (e.g., WL) method, in which an instrument, including tools and/or sensors for analyzing the geological formation, is lowered into the borehole after the borehole has been drilled.

Non-limiting examples of one or more tools and sensors for analyzing the geological formation sample include a neutron-gamma-ray spectroscopy tool, an ionization mass spectrometry (MS) tool, an X-ray fluorescence spectroscopy (XRF) tool, a Raman spectroscopy tool, a laser-induced breakdown spectroscopy (LIBS) tool, an atomic absorption spectroscopy (AAS) tool, an atomic emission spectroscopy (AES) tool, an induced-neutron activation (INA) tool, a bulk density tool, a nuclear magnetic resonance (NMR) tool, an electromagnetic resistivity tool, and a dielectric tool.

The neutron-gamma spectroscopy tool can be designed to emit neutrons into the geological formation sample and detect a spectra of gamma rays that result when the neutrons interact with the elements of the geological formation. Interactions between the components of the geological formation and the neutrons may produce gamma rays in at least two ways: inelastic scattering and neutron capture. Inelastic scattering occurs when fast neutrons collide with the elements of the formation, which can result in the emission of one or more gamma rays. Neutron capture occurs when lower-energy thermal or epithermal neutrons are captured by the nuclei of elements of the formation, which also may result in the emission of one or more gamma rays. In either case, the various energies of the resulting gamma rays can be detected by gamma ray detectors in the downhole tool to obtain gamma-ray spectrum measurements. The spectra of gamma rays obtained at various depths in the well (e.g., borehole) can be used to ascertain a variety of different well properties.

The neutron porosity tool can be designed to direct a source of neutrons into the geological formation and then detect a scattered signal of the neutrons interacting with the elements of the geological formation. The source of neutrons can be generated from an electronic pulsed neuron generator or a radio-chemical source of neutrons from nuclear decays.

The bulk density tool can include a source or generator for producing X-rays or gamma rays (e.g., an electronic generator of X-rays or a radio-chemical source of gamma rays from nuclear decays) and a sensor for sensing a scattered signal of the X-rays or gamma rays. The intensity of the sensed scattered signal can be used to determine an approximate bulk density of the geological formation sample.

The NMR tool can be designed to align the protons of a hydrogen nuclei with a magnetic field and to cause the protons to precess with an electromagnetic signal. The decay of the resulting signal from the protons can be used to determine the hydrogen content, a pore volume, a pore size distribution, pore surface area, one or more fluid types and fluid properties, and other aspects of the geological formation.

In other examples, the geological formation sample is collected from the geological formation through the borehole, brought to the surface, and analyzed at the surface via the one or more tools or sensors described herein.

Determining the Reactivity of One or More Minerals Present Within a Geological Formation Provided herein are methods of determining the reactivity of one or more minerals present within a geological formation within a target zone in response to the injection of $CO_2$ into the target zone.

For example, the methods may comprise one or more of the following steps: (1) determining one or more mineral and fluid characteristics of a geological formation comprising one or more minerals; (2) using a reaction rate model to characterize the chemical reactivity of one or more minerals present in a target zone of the geological formation in response to injection of $CO_2$ into the target zone; (3) using a reactivity index model to estimate the amount of one or more minerals in the target zone that would be modified between a first time point and a second point during a $CO_2$ injection and sequestration operation; and (4) injecting an amount of $CO_2$ into the target zone based on the estimated reactivity of the one or more minerals present in the target zone. Each of these steps is discussed in further detail below.

Determining One or More Mineral and Fluid Characteristics of a Geological Formation The methods provided herein may comprise, for example, determining one or more mineral and fluid characteristics of a geological formation. For example, the methods may comprise determining one or more geological formation inputs using the one or more of the sample collection and analysis techniques described in detail above.

Characterizing the Chemical Reactivity of the Geological Formation to $CO_2$ Injection The methods provided herein may comprise, for example, using a reaction rate model to characterize the chemical reactivity of the geological formation to a $CO_2$ injection.

Chemical reactions between aqueous and solid phases do not generally occur instantaneously but are rate limited. Thus, determining a set of metrics for characterizing the chemical reactivity (e.g., the mineral reaction rate expression) of a geological formation to a $CO_2$ injection is based on the principles of chemical kinetics. Accordingly, the kinetically controlled mineral dissolution and precipitation within the geological formation can be defined by Formula 8.

$$\left(\frac{\mathrm{dm}}{dt}\right)_i = \pm k_i A_i \left|1 - \left(\frac{Q}{K}\right)^{p_i}\right|^{q_i} \quad \text{Formula 8}$$

wherein,

- dm/dt is the reaction rate for a mineral i (e.g., defined by moles per unit time);
- $k_i$ is a temperature-dependent rate constant (e.g., defined by moles per unit mineral surface area per unit time);
- $A_i$ is a mineral specific reactive surface area (e.g., unit surface area);
- Q is an ion activity product (e.g., a dimensionless value);
- $p_i$ and $q_i$ are empirical parameters and are unitless. In some examples, $p_i$ and $q_i$ are unknown experimentally, therefore, $p_i$ and $q_i$ can be equal to one; and
- K is a solubility product (e.g., a dimensionless value). More particularly, K is a thermodynamic equilibrium constant for the dissolution of a solid phase into an aqueous solution (commonly denoted. $K_{sp}$).

Determining the Solubility Product, K of Formula 8

In some examples, the solubility product values for the minerals being analyzed can be determined from technical literature such as scientific papers. In other examples, the solubility product values for the minerals being analyzed can be determined using the systems and techniques described herein.

In some examples, K can be described by Formula 9.

$$\alpha Z(s) \leftrightarrow \beta X(aq) + \gamma Y(aq);\ K_{sp} = \{X\}^{\beta}\{Y\}^{\gamma} \quad \text{Formula 9}$$

wherein,

- Z, X, and Y are symbols denoting the chemical species involved in the reaction;
- α, β, and γ are mole coefficients for the species (e.g., Z, X, and Y) in the reaction; and
- (s) and (aq) refer to the phase of the species (e.g., Z, X, and Y) in the reaction.

Determining the Ion Activity Product, Q of Formula 8

In some examples, Q can be determined with knowledge of the aqueous solution composition of the geological formation. Thus, the ion activities can be assumed to be the same as those of the measured concentrations in the geological formation sample. Further, in some examples, full geochemical speciation calculations can be applied to account for non-idealized behavior in saline solutions (e.g., activity coefficients that deviate from unity In some examples, Q can be determined by a formula similar to Formula 9. However, the input aqueous species concentrations are the actual free species activities in the solution for which reaction rates are being computed, not the aqueous species equilibrium activities used to determine the solubility product value.

The logarithmic ratio of Q (e.g., the ion activity product) divided by K (the solubility product) is known as a saturation index Ω.

Determining the Temperature-Dependent Rate Constant, $k_i$ of Formula 8

The temperature-dependence of $k_i$ can be approximated by Formula 10.

$$k_i = k_i^x \exp\left[\frac{E_a}{R}\left(\frac{1}{T} - \frac{1}{298.15}\right)\right] \quad \text{Formula 10}$$

wherein, $$k_i^x$$

is the reaction rate constant at various conditions;

$E_a$ is the activation energy for the reaction (e.g., expressed in Joules per mole);

R is the ideal gas constant (e.g., 8.3145 Joules per mole per Kelvin); and

T is a reaction temperature (e.g., expressed in units of Kelvin).

$$k_i^x$$

can be based on one or more conditions, including temperature, pH value, and concentration of various aqueous species of the geolocial formation.

For example, $$k_i^x$$

can be the reaction rate constant at 25° C. (e.g., 298.15 K).

In another example, $$k_i^x$$

can be calculated as a value corresponding to a reaction temperature equal to the geological formation's temperature, according to the temperature-dependence of the rate constant expressed by the Arrhenius relationship $$\left(\text{i.e., } k_i^x = k_i^{T=geological\ formation}\right).$$

The geological formation temperature can be obtained from the temperature measurements made within a borehole traversing the geological formation using the systems and methods described herein, as well as other known techniques in the art.

In yet another example, $$k_i^x$$

can be adjusted to account for cooling effects on the geogical formation from expansion of $CO_2$ upon entry of the $CO_2$ into the geological formation (e.g., Joule-Thomson effect). The cooling effects or resulting formation temperature may be estimated from thermodynamic calculations known in the art, combined with knowledge of pressure in the well bore and formation, or from direct measurements of formation temperature during $CO_2$ injection operations.

In still another example, $$k_i^x$$

can be based at least partially on a pH value of a formation fluid. The formation fluid can include naturally occurring water or other fluids present within the porous spaces of the geological formation.

For instance, $$k_i^x$$

can be determined using the rate constant associated with a neutral reaction (e.g., $$k_i^x = f(k_{i,neutral})).$$

This approach is generally applicable for aqueous pH values within 1 to 2 units on either side of neutrality. The formation fluid can be assumed to be pure water having a fixed pH value at a temperature of 25° C. (e.g., pH=7, $aH^+=10^{-7}$). Alternatively, the pH value can be assumed to vary according to the geological formation temperature. In the case that pH value is assumed to vary, $$k_i^x$$

can be simplified to a function of only the reaction rate constant for the neutral mechanism (e.g., $k_{i,neutral}$) and specific reactive surface area. Accordingly, the ion activity product Q can be assigned a value of zero.

In another instance, $$k_i^x$$

can be determined using rate constants associated with at least one of an acid or base reactions (e.g., $$k_i^x = f(k_{i,acid}, k_{i,base})).$$

Thus, $$k_i^x$$

can be adjusted according to the formation fluid's pH value. The formation fluid's pH value can be determined with knowledge of the solubility of $CO_2$ in the formation fluid. The $CO_2$ solubility is a function of temperature, pressure, and solution ionic strength (e.g., approximately equal to a chlorinity value of the formation fluid), which can be determined from borehole logging measurements. Thus, $$k_i^x$$

can be a function of the reaction rate constants for acid, neutral, and base reaction mechanisms, $k_i=f(k_{i,neutral}, k_{i,acid}, k_{i,base})$.

In another example, $$k_i^x$$

can be based at least partially on the concentrations of one or more aqueous species before $CO_2$ injection. The concentrations of the one or more aqueous species can be estimated from an assumption of equilibrium between the formation fluid and the minerals of the geological formation. As discussed herein, the mineralogy of the geological formation can be determined from borehole logging measurements or other measurements performed on a sample of the geological formation.

Water properties, including temperature, pressure, salinity, chlorinity, and concentrations of other elements, can be estimated from downhole measurements of the borehole. In this instance, the ion activity product Q can be estimated from these aqueous species concentrations.

Alternatively, the water properties can be determined by analyzing an initial formation fluid sample according to standard laboratory techniques designed to determine concentrations of the one or more aqueous species in the formation fluid. Thus, the concentrations of the one or more aqueous species in the formation fluid can be used to determine an approximate mineral reaction rate constant (e.g., $$k_i^x$$

and ion activity product (e.g., Q of Formula 8) for each mineral present in the geological formation that is being analyzed. Thus, $$k_i^x$$

can be determined as a function of the magnitude of a chemical disequilibrium between the geological formation minerals and the formation fluids, wherein the aqueous composition may refer to the aqueous composition and pH after the $CO_2$ has fully dissolved in the formation fluid.

In yet another example, $$k_i^x$$

and $E_a$ can be drawn from technical literature.

Further, extensions of the reaction rate constant to consider catalysis by aqueous species are done by multiplying Formula 10 with Formula 11.

$$\prod_j a_j^{n_j} \qquad \text{Formula 11}$$

wherein, $a_j$ is the activity of aqueous species; and j and n are the stoichiometric coefficient for the reaction at hand.

In some examples, $H^+$ (e.g., an acid mechanism) and $OH^-$ (e.g., a basic mechanism) are the modeled aqueous species. Thus, the chemical reaction can be pH dependent.

In some examples, pH dependency can be characterized using Formula 10, for acid, neutral, and basic mechanisms, wherein the $k_i^x$ and $E_a$ value are determined as described herein.

In some examples, the $k_i^x$ and $E_a$ values for acidic and basic mechanisms are not known. Thus, only the neutral mechanism is used.

Determining the Mineral Specific Reactive Surface Area, $A_i$ of Formula 8

The mineral specific reactive surface area $A_i$ is dependent on grain factors such as shape (e.g., spheric, cubic, tabular), diameter, packing density, and porosity of the geological formation. Thus, in some examples, the mineral specific reactive surface areas $A_i$ are determined according to the mineral's characteristic geometric properties (size and shape).

In some examples, $A_i$ can be held constant (e.g., not recomputed) during reaction calculations.

In some examples, $A_i$ can be determined from literature. A non-limiting example includes Wentworth's 1922 classification of grades in clastic sediments, where clay minerals can be defined as having a grain size of less than or equal to about 2 μm and sand grains can be defined as having a grain size within about 63 μm to about 2 mm.

In another example, $A_i$ can be determined from known geometric relationships. For example, Formula 12 illustrates the entire surface area of a sphere (e.g., $G_{sphere,i}$) in relation to the radius of the sphere (e.g., $r_i$).

$$G_{sphere,i} = 4\pi r_i^2 \qquad \text{Formula 12}$$

wherein, $G_i$ is the geometric area for a single grain of the geological formation.

Similar relationships apply to other geometric units like cuboids, cylindrical columns, hexagonal columns, and the like. However, the entire surface area of the mineral may not be available for reaction. Thus, in some examples, a geometric surface area (e.g., in reference to a single grain) can be transformed to a specific surface area (e.g., in reference to the total amount of a mineral) using conversions known in the art.

In other examples, proportionality or scaling factors can be applied to reduce a specific surface area to a mineral-specific reactive surface area, accounting for grain-to-grain contacts that lower the aqueous phase access to mineral surfaces for reaction. Thus, the mineral specific reactive surface area $A_i$ can be a fixed value in some assigned proportion to its geometric area $G_i$.

In yet another example, a specific reactive surface area can be defined as the mineral surface area with respect to an additional formation data parameter.

Non-limiting examples of the additional formation data parameter include a mass of the mineral (e.g., $m^2/g$), a number of moles (e.g., $m^2/mol$) of the mineral, or a unit volume of geological formation sample (e.g., $m^2/m^3$).

In yet another example, a mineral-specific reactive surface area can be measured directly, using standard laboratory techniques like gas-adsorption surface area analysis.

Using a Reactivity Index Model to Estimate the Effects of $CO_2$ Injection

The methods provided herein may comprise using a reactivity index model to estimate the amount of one or more minerals that will be modified between a first time point and a second point during a $CO_2$ injection and sequestration operation. For example, information determined during a preceding step of the method can be used to determine the amount of one or more minerals modified between a first time point and a second point during a $CO_2$ injection and sequestration operation.

The fraction of the geological formation dissolved can be described as a sum amount of all of the minerals dissolved at a given point in time (e.g., t=n, where n>0) divided by an initial amount of the minerals or geological formation present at an initial or first point in time (e.g., t=0). This fraction can be labeled as a reactivity index.

The reactivity index may also be directed toward a fraction of the formation that is created due to the precipitation of minerals, instead of dissolution. Minerals and chemical species for Formulas 8 and 9 may be selected with an appropriate definition of kinetic rate $k_i^x$ to estimate the rate of mineral precipitation, which may also be included in the reactivity index. In the discussion herein, references to mineral dissolution may also be considered to include processes of mineral precipitation.

The reactivity index can be defined in units of moles, mass, or volume. Further, if the reactivity index is defined by one unit, the reactivity index can be converted to another unit of measure. For example, a mineral volume-fraction can be determined from a mineral mass-fraction if the mineral grain density is known. In another example, a mineral mole-fraction can be determined from a mineral mass-fraction if the mineral molecular weight is known.

Thus, in some examples, the third step of the method includes defining a reactivity index metric for determining a value that represents a fraction of the geological formation that is dissolved or precipitated at a given point in time, beginning from the injection of $CO_2$ into the geological formation.

The reactivity index can be at least partially based on the time-dependent reaction rate described by Formula 8.

The reactivity index can be further based on one or more of the geological formation inputs described herein. For example, the reactivity index can be at least partially based on an initial mineralogical assemblage in the geological formation. Thus, the third step of the method can include determining the mineral make-up of the geological formation according to the systems and methods described herein.

In one example, the reactivity index is an estimate of a relative change in a total mineral volume induced by the presence of $CO_2$ with respect to an original mineral volume, summed over a plurality of mineral reactions and integrated over a specified time duration. Thus, the reactivity index (RI) can be determined according to Formula 13.

$$RI = \frac{1}{(1-\phi)} \sum_{time\ t_j=0}^{t^{max}} \left[ \sum_{mineral\ i}^{selected} \frac{dm_i(t_j)}{dt} \cdot \frac{M_i}{\rho_i} \right] \Delta t_j \quad \text{Formula 13}$$

wherein, the reaction rate $$\frac{dm_i(t_j)}{dt}$$

is determined according to Formula 8;

i represents a particular mineral and is determined for a mineral molar concentration $m_i(t_j)$ at one or more time steps $t_j$;

$M_j$ is a volume conversion defined by a molar mass (e.g., mass per mole) and a mass density, $\rho_i$ (e.g., mass per volume) for the mineral i;

$\phi$ is the initial porosity of the geological formation within the target zone (e.g., pre-injection at $t_j$=0) that provides the normalization with respect to the original volume of minerals; and $t_{max}$ is a maximum time duration. In some examples, $t_{max}$=0 (e.g., the reactivity index represents an initial rate).

The reactivity index can be determined over any set of selected minerals (including a subset or all of the minerals present in the rock) and over any time duration with any definition of time steps $\Delta t_j$.

Thus, in some examples, the reactivity index is defined with respect to all of the minerals present in the geological formation.

In other examples, the reactivity index is defined with respect to less than all of the minerals (e.g., i) present in the geological formation. For instance, accessory minerals (e.g., minerals that are present in low-to-trace abundance) can be disregarded.

In some examples, the reactivity index is determined according to multiple instantaneous mineral reaction rates, including a first mineral reaction rate at the beginning of the $CO_2$ injection operation (e.g., a first time point where $t_j$=0 according to Formula 8) and a second mineral reaction rate at a specified length of time for the reaction (e.g., a second time point where $t_j$=n, wherein n is a value representing a time period (e.g., hours, days, years) from the beginning of the $CO_2$ injection operation). Thus, the amount of the mineral dissolved can be described by a linear extrapolation or by an integral of the instantaneous reaction rate at time zero (e.g., $t_j$=0) with respect to a time interval (e.g., $t_j$=n). In some examples, the total time interval may be defined such that the reactivity index represents an instantaneous rate of change in mineral volumes.

In some examples, the reactivity index is calculated using mineral reaction rates that change (e.g., a nonlinear rate) as a function of time in response to a changing mineral phase and an aqueous phase equilibria (e.g., a changing value of the ratio Q/K described in Formula 8). Thus, the amount of the mineral dissolved can be described by a nonlinear extrapolation or an integral of the time-dependent reaction rate with respect to a time interval (e.g., $t_j$=n), or is equal to the amount of mineral dissolved at each time-step when the time interval is discretized into multiple smaller time-steps having a defined reaction rate.

In another example, the reactivity index can be normalized with respect to a pore volume, such that the reactivity index represents a relative change in porosity induced by the presence of $CO_2$. Thus, the reactivity index can be determined according to Formula 14.

$$RI = \frac{1}{\phi} \sum_{time\ t_j=0}^{t^{max}} \left[ \sum_{mineral\ i}^{selected} \frac{dm_i(t_j)}{dt} \cdot \frac{M_i}{\rho_i} \right] \Delta t_j \quad \text{Formula 14}$$

wherein, the reaction rate $$\frac{dm_i(t_j)}{dt}$$

is determined according to Formula 8;

i represents a particular mineral and is determined for a mineral molar concentration $m_i(t_j)$ at one or more time steps $t_j$;

$M_i$ is a volume conversion is defined by a molar mass, (e.g., mass per mole) and a mass density, $\rho_i$ (e.g., mass per volume) for the mineral i;

$\phi$ is the initial porosity of the geological formation within the target zone (e.g., pre-injection at $t_j$=0) that provides the normalization with respect to the original volume of minerals; and $t_{max}$ is a maximum time duration. In some examples, $t_{max}$=0 (e.g., the reactivity index represents an initial rate).

In other examples, the reactivity index can be defined without any normalization relative to porosity, such that the reactivity index represents an absolute change or rate of change in mineral volume.

Injecting $CO_2$ Into a Target Zone of a Geological Formation

The methods provided herein may comprise injecting an amount of $CO_2$ into a target zone of a geological formation based on the estimated reactivity of one or more minerals present in the target zone. For example, the methods may comprise injecting $CO_2$ in a target zone of a geological formation based on the determined reactivity index of one or more geological formation samples.

As previously discussed herein, a reactivity index can be determined for one or more geological formation samples. Each geological formation sample can correspond to a particular zone of a geological formation. For example, a first sample can correspond to a first zone of the geological formation at a first depth range of a borehole. Similarly, a second sample can correspond to a second zone of the geological formation at a second depth range that is different than the first depth range of the borehole.

The geological formation can be split into one or more zones based on one or more thermophysical, geophysical, and geochemical properties of the geological formation. As discussed herein, non-limiting examples of thermophysical, geophysical, and geochemical properties include a mineral make-up, one or more mineral concentrations (e.g., mole fraction, mass fraction, or volume fraction), a mineral surface area, a pore volume, a pore surface area, a pore-size distribution, an electromagnetic resistivity, one or more dielectric properties, imaging data, a gas concentration, and acoustic properties of the geological formation, and a pH value of the formation fluid of the geological formation. Further, in some examples, a mineral specific reactivity index can be used to determine the one or more zones.

The reactivity indexes for each sample can be compared to determine the target zone for a CCS operation. For example, the determined reactivity index of the second sample can indicate that the zone of the geological formation associated with the second sample is better suited for $CO_2$ injection as compared to the zone of the geological formation associated with the first sample. Thus, the zone of the geological formation associated with the second sample can be the target zone for a CCS operation.

Accordingly, the method includes sequestering captured $CO_2$ in the target zone. The captured $CO_2$ can be compressed into a fluid and transported to the target zone field location. The compressed $CO_2$ is injected into the target zone and then trapped for storage.

Non-limiting examples of systems and processes for trapping the compressed $CO_2$ in the geological formation include structural trapping, residual trapping, dissolution trapping, and mineralization.

In structural trapping, the injected CO2 is trapped within structural features of the geological formation, such as faults, folds, or caprock formations, which can act as impermeable barriers preventing $CO_2$ migration after injection.

In residual trapping, the injected $CO_2$ remains trapped within the pore spaces of the geological formation due to capillary forces and interfacial tension, thereby preventing the release of the injected $CO_2$.

In dissolution trapping, the injected $CO_2$ can dissolve into the formation fluid over time, increasing the density of the formation fluid or reducing the buoyancy of the $CO_2$, effectively immobilizing the $CO_2$ within the geological formation.

In mineralization, the injected $CO_2$ can react with minerals in the geological formation to form stable carbonate minerals or other minerals which can trap the injected $CO_2$ in a solid form.

During and/or after the injection and trapping of the $CO_2$ the target zone can be monitored to confirm that the sequestration operation is successful. Monitoring techniques for analyzing the success of the sequestration operation can include seismic surveys, pressure monitoring, pulsed neutron logs or other wellbore measurements, groundwater monitoring, and geochemical analysis to track $CO_2$ migration, assess the target zone performance, and detect potential leakage risks.

Further, in some examples, the reactivity index can be used to determine a target pressure of the injection fluid, a target injection flow rate, and/or a target purity or compositional mixture of the injected $CO_2$.

EXAMPLES

The following non-limiting example is provided to further illustrate the present disclosure.

Example 1

FIG. 1 shows an example of using a reactivity index derived from borehole measurements to select one or more target zones for a CCS operation. More particularly, FIG. 1 compares various thermophysical, geophysical, and geochemical properties of a geological formation and various mineral specific reactivities for minerals included in the geological formation along a depth of a borehole drilled in the geological formation.

Specifically, a temperature, a porosity, a gas concentration, a pH value, a mineral volume, a carbonate reactivity (e.g., a change in carbonate volume fractions per unit time), a quartz reactivity (e.g., a change in quartz volume fractions per unit time), a feldspar reactivity (e.g., a change in feldspar volume fractions per unit time), and a reactivity index determined according to Formula 14 are compared along the depth of the borehole. In this case, the reactivity index is designed to represent the relative change in porosity per day when $CO_2$ is first introduced into the geological formation.

As shown, the depth of the borehole is divided into a plurality of zones. Here, six zones are determined based on detected changes in the temperature, the porosity, the gas concentration, the pH value, the mineral volume, the carbonate reactivity, the quartz reactivity, the feldspar reactivity, and/or the reactivity index along the depth of the borehole.

It can be seen that that zones containing proportionally more carbonate and feldspar react more strongly with an aqueous $CO_2$ solution. Further, the effect $CO_2$ injection has on the reactivity index varies depending on the water composition, the porosity, the gas saturation, the temperature, and other factors. Thus, it can be determined that zone 1 may be the preferred target zone for a CCS operation.

When introducing elements of the present disclosure or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the disclosure are achieved and other advantageous results attained.

Further, various changes could be made in the above products and methods without departing from the scope of the disclosure, it is intended that all matter contained in the above description shall be interpreted as illustrative and not in a limiting sense.

What is claimed is:

1. A method for determining a reactivity of one or more minerals present within a geological formation within a target zone in response to an injection of $CO_2$ into the target zone, the method comprising:

determining one or more mineral and fluid characteristics of the geological formation comprising the one or more minerals;

using a reaction rate model to characterize a chemical reactivity of the one or more minerals present in the target zone of the geological formation in response to the injection of $CO_2$ into the target zone;

using a reactivity index model to estimate an amount of the one or more minerals in the target zone that would be modified between a first time point and a second point during a $CO_2$ injection and sequestration operation; and injecting an amount of $CO_2$ into the target zone based on the chemical reactivity of the one or more minerals present in the target zone, wherein the reactivity index model comprises Formula 14, wherein:

$$RI = \frac{1}{\phi} \sum_{time\ t_j=0}^{t^{max}} \left[ \sum_{mineral\ i}^{selected} \frac{dm_i(t_j)}{dt} \cdot \frac{M_i}{\rho_i} \right] \Delta t_j \quad \text{Formula 14}$$

i represents a particular mineral of said one or more minerals, and is determined for a mineral molar concentration $m_i(t_j)$ at one or more time steps $t_j$;

$$\frac{dm_i(t_j)}{dt}$$

is a reaction rate for the mineral i, expressed in moles per unit time;

$M_i$ is a volume conversion defined by a molar mass and a mass density for the mineral i;

$\phi$ is an initial porosity of the geological formation within the target zone that provides a normalization with respect to an original volume of minerals; and $t_{max}$ is a maximum time duration.

2. The method of claim 1, wherein the reactivity index model models a change in mineral volumes that represents a fractional change or an absolute change with respect to the geological formation.

3. The method of claim 1, wherein the amount of the one or more minerals in the target zone that is modified is an amount of the one or more minerals that dissolves during the $CO_2$ injection and sequestration operation.

4. The method of claim 1, wherein the amount of the one or more minerals in the target zone that is modified is an amount of the one or more minerals that precipitates during the $CO_2$ injection and sequestration operation.

5. The method of claim 1, further comprising determining at least one of a target pressure of the injected $CO_2$, a target injection flow rate of the injected $CO_2$, and a target purity or compositional mixture of the injected $CO_2$ based on the reactivity index model.

6. The method of claim 1, wherein the first time point and the second point during the $CO_2$ injection and sequestration operation are the same point in time.

7. The method of claim 1, wherein the first time point and the second point during the $CO_2$ injection and sequestration operation are different points in time.

8. The method of claim 1, wherein the reactivity index model is defined with respect to all of the one or more minerals in the geological formation.

9. The method of claim 1, wherein the reactivity index model is defined with respect to less than all of the one or more minerals in the geological formation.

10. The method of claim 1, wherein the reactivity index model is at least partially based on one or more formation fluid characteristics of a formation fluid included in the geological formation, where the one or more one formation fluid characteristics are selected from the group consisting of a temperature, a pressure, a salinity, a chlorinity, a pH, and a concentration of aqueous an ion species of the formation fluid.

* * * * *